United States Patent [19]
Iffland et al.

[11] Patent Number: 5,883,288
[45] Date of Patent: Mar. 16, 1999

[54] CONTINUOUS PREPARATION OF ALKYL ESTERS OF (METH)ACRYLIC ACID

[75] Inventors: Gabriele Iffland, Marl; Albrecht Dams, Wachenheim; Alexander Weck, Bühlertal; Heinrich Aichinger, Mannheim; Holger Herbst, Frankenthal; Gerhard Nestler, Ludwigshafen; Herbert Exner, Waldsee; Willi Schmidt, Ludwigshafen; Matthias Geisendörfer, Neustadt; Toni Dockner, Meckenheim, all of Germany

[73] Assignee: BASF Aktiengesellschaft, Ludwigshafen, Germany

[21] Appl. No.: 791,052

[22] Filed: Jan. 28, 1997

[30] Foreign Application Priority Data

Feb. 6, 1996 [DE] Germany ................. 196 04 267.4

[51] Int. Cl.$^6$ .................................................. C07C 69/52
[52] U.S. Cl. ............................................... 560/205
[58] Field of Search ............................. 560/205

[56] References Cited

U.S. PATENT DOCUMENTS

| | | |
|---|---|---|
| 4,280,009 | 7/1981 | Erpenbach et al. . |
| 4,280,010 | 7/1981 | Erpenbach et al. . |
| 4,739,108 | 4/1988 | Lillwitz . |

FOREIGN PATENT DOCUMENTS

| | | |
|---|---|---|
| 0 733 617 | 9/1996 | European Pat. Off. . |
| 25 48 561 | 5/1977 | Germany . |
| 25 52 987 | 6/1977 | Germany . |
| 0 017 522 | 1/1966 | United Kingdom . |
| 1 173 118 | 12/1969 | United Kingdom . |

*Primary Examiner*—Paul J. Killos
*Attorney, Agent, or Firm*—Oblon, Spivak, McClelland, Maier & Neustadt, P.C.

[57] ABSTRACT

In the process for the continuous preparation of alkyl esters of (meth)acrylic acid by reacting (meth)acrylic acid with monohydric alkanols having from 1 to 8 carbon atoms in the presence of an acid esterification catalyst in a reaction zone, there is discharged from the reaction zone a product mixture which comprises the alkyl (meth)acrylate formed, the catalyst and the by-products formed during the course of the esterification having boiling points higher than that of the alkyl (meth)acrylate, and from which the alkyl (meth)acrylate is separated by distillation in a separation zone. The product mixture discharged from the reaction zone is fed to a rectification unit (I), in this unit the product mixture discharged is separated by rectification into at least one product (I) comprising the alkyl ester of (meth)acrylic acid and a product (II) comprising the catalyst, the product (I) is fed to a further rectification unit (II) and in this the alkyl ester of (meth)acrylic acid is separated off by rectification.

18 Claims, 2 Drawing Sheets

CONTINUOUS PREPARATION OF ALKYL ESTERS OF (METH)ACRYLIC ACID

The present invention relates to a process for the continuous preparation of alkyl esters of (meth)acrylic acid by reacting (meth)acrylic acid with monohydric alkanols having from 1 to 8 carbon atoms in the presence of an acid esterification catalyst.

The term (meth)acrylic acid here refers, as is customary, to acrylic or methacrylic acid. In esterifications of an alkanol with an organic acid, typical equilibrium reactions generally proceed, these reactions being catalyzed by strong acids and, as typical condensation reactions, leading to elimination of water. The esterification equilibrium is usually shifted in the desired direction by removal of the water from the reaction mixture. The removal of the water can be carried out by distillation as constituent of an azeotrope comprising the target ester. The continuous removal of the reaction water from the reaction mixture is simultaneously accompanied by the separation of the target ester from the reaction mixture. In general, the esterification reaction proceeds with the water being removed continuously from the reaction mixture, but the major amount of the target ester formed remains in the reaction mixture.

Examples of esterifications of this type are those in which the water of reaction is distillatively removed by addition of an organic solvent as azeotropic entrainer. However, (starting) alkanol used in excess can also serve as such an azeotropic entrainer. In another variant, the water is distillatively removed as constituent of an azeotrope comprising target ester/alkanol/water and containing more than 95% by weight of water.

The product mixtures formed in such esterifications contain essentially excess alkanol, excess (meth)acrylic acid, acid esterification catalyst and polymerization inhibitors, since (meth)acrylic acid and their esters tend to polymerize. In addition, azeotropic entrainers or organic solvents, residual amounts of water and high-boiling by-products (Michael adducts) may also be present. The target ester then has to be separated from these product mixtures. According to Ullmann's Encyclopedia of Industrial Chemistry, 5th edition, Vol. A1, VCH Weinheim, pages 168–169, this separation is generally carried out by the product mixture first being washed with water. The acid esterification catalyst and the excess (starting) acid go from the organic product phase into the aqueous phase and are thus removed from the product mixture. The separation is normally completed by further washing with aqueous alkali solution.

Subsequently, the remaining alkanol is, as a rule, first removed from the remaining organic phase in a first rectification column and the target ester is then separated off in a further rectification column, in each case via the top of the column.

The disadvantage of such a work-up procedure is, in particular, the formation of large amounts of greatly contaminated wastewater. In addition, the acid dissolved in the aqueous alkali solution and the alkanol dissolved therein can generally not be returned directly and technically simply to the esterification, which causes losses of starting materials.

A water-free work-up process is known, for example, from DE-C 25 48 561 for the preparation of 2-ethylhexyl acrylate. In the work-up procedure described therein, excess alkanol and excess acid are separated from the product mixture by distillation via the top of the column. In a downstream distillation column, the target ester is then separated by distillation from the bottom product of the preceding distillation column. However, the bottom product from which the target ester is separated by distillation still contains the acid catalyst of the actual esterification reaction. In addition, the distillative separation of the target ester requires elevated temperatures even under reduced pressure. This leads to redissociation of the Michael adducts formed as by-products in the actual esterification occurring during the distillative separation. The redissociation then forms alkanol having a boiling point lower than that of the target ester plus acid and also olefins, which may have a low boiling point, which result from water elimination from the alkanol and are then present as impurities in the target ester separated off by distillation. The purity of a target ester obtained in this way is unsatisfactory.

GB-B 1 017 522 discloses a process for preparing n-butyl acrylate. As esterification conditions, this describes a certain molar ratio of (starting) alkanol to (starting) acid and a content of catalytically active acid of from 0.5 to 5% by weight, based on the total mass of the reactants. Disadvantages of this procedure are the high excess of alkanol required, which promotes the formation of undesired dialkyl ethers, and the not fully satisfactory yield of n-butyl acrylate under the abovementioned conditions, based on the amount of acrylic acid used.

DE-C 25 52 987 discloses a process for the continuous preparation of alkyl esters of acrylic acid by reacting acrylic acid and monohydric alkanols having from 1 to 4 carbon atoms in a molar ratio of from 1(alkanol):1(acrylic acid) to 2(alkanol):1(acrylic acid) in a homogeneous, liquid, solvent-free phase at elevated temperature and in the presence of sulfuric acid or organic sulfonic acid as catalyst, in which the acrylic acid, the alkanol and the acid catalyst are fed continuously into a reaction zone the alkyl acrylate formed is separated off by rectification, during a residence time of several hours as constituent of at least one aqueous azeotrope comprising, apart from the alkyl acrylate, water or water and alkanol as further constituent via the top of a rectification column superposed on the reaction zone, the distillate I obtained is separated into an organic phase comprising the acrylic ester formed and an aqueous phase, part of the organic phase is, for the purpose of producing an increased separation action, returned to the rectification zone via the top and, if desired, part of the aqueous phase is returned to the rectification zone via the top to maintain the composition of the aqueous azeotrope, the alkyl ester is separated in a manner known per se from the excess organic phase and part of the reaction mixture is discharged from the reaction zone, freed of high boilers by distillation and the distillate thus obtained is returned to the reaction zone.

The primary objective here is the avoidance of undesired ether formation from (starting) alkanol. However, a disadvantage of this procedure is that, despite distillative treatment of the discharge from the reaction mixture and the return of the distillate thus obtained to the reaction zone, the yield of alkyl acrylate, based on acrylic acid used, is not satisfactory. The reduction achieved in the dialkyl ether by-product formation is also not fully satisfactory. Furthermore, the residence time required according to the examples is also not satisfactory. This also applies to the space-time yield. It is assumed that this is caused by the low concentration of acid esterification catalyst.

It is an object of the present invention to provide a process for the continuous preparation of alkyl esters of (meth)acrylic acid which makes possible not only an optimized yield but also milder reaction conditions and thus, besides greatly reduced ether formation, less formation of high boilers, a high space-time yield, increased flexibility in the operation of the plant and also low capital costs owing to a minimized number of equipment items.

We have found that this object is achieved starting with the known process for the continuous preparation of alkyl esters of (meth)acrylic acid by reacting (meth)acrylic acid with monohydric alkanols having from 1 to 8 carbon atoms in the presence of an acid esterification catalyst in a reaction zone, in which there is discharged from the reaction zone a product mixture which comprises the alkyl (meth)acrylate formed, the catalyst and the by-products formed during the course of the esterification having boiling points higher than that of the alkyl (meth)acrylate, and from which the alkyl (meth)acrylate is separated by distillation in a separation zone. The inventive process is characterized by feeding the product mixture discharged from the reaction zone to a rectification unit I, in this unit separating the product mixture discharged by rectification into at least one product I comprising the alkyl ester of (meth)acrylic acid and a product II comprising the catalyst, feeding the product I to a further rectification unit II and in this separating off the alkyl ester of (meth)acrylic acid by rectification.

Both here and below, the term rectification unit is used as a general designation for apparatuses in which heat input generates vapors which rise and are in contact with liquid phase flowing downward. These also include simple distillation columns. However, these are generally rectification columns having internal fittings to provide efficient contact between liquid and vapor. Such internal fittings are trays such as bubble cap trays, perforated trays, in particular dual flow trays, beds, packings or the like. To simplify the understanding of the relationships, the various rectification units are designated by Roman numerals. The various, specifically described products are also designated in this way.

Thus, according to the present invention, the product mixture discharged from the reaction zone is separated by rectification in a first rectification unit I into at least one product I comprising the alkyl (meth)acrylate to be isolated, which product I can be taken from the upper part of the rectification unit I, plus a product II which is formed in the lower part of the rectification unit I and comprises the catalyst. The product I comprising the alkyl ester of (meth) acrylic acid and taken off in the upper part of the rectification unit I is fed to a further rectification unit II and in this the pure alkyl (meth)acrylate to be isolated is then separated off by rectification.

According to an advantageous embodiment of the present invention, the esterification in the reaction zone takes place in a homogeneous, liquid, solvent-free phase at elevated temperature by reaction of (meth)acrylic acid and the monohydric alkanol in a molar ratio of from 1:0.75 to 1:2, preferably from 1:0.9 to 1:1.1, particularly preferably in a ratio of 1:1. Here, the (meth)acrylic acid, the alkanol and the catalyst are fed to the reaction zone and the water formed is removed by rectification during a residence time as constituent of a mixture comprising alkanol via the top of a rectification unit III superposed on the reaction zone. The distillate thus obtained is separated into an organic phase comprising starting alkanol and an aqueous phase comprising water. The organic phase and, if desired, aqueous phase are returned to the rectification unit III. The reaction mixture thus largely freed of water is discharged from the reaction zone and fed to a separation zone.

The reaction zone consists of one or more reaction regions. In an embodiment of the invention having a plurality of reaction regions, it is advantageous to cascade these. The liquid output stream of one reaction region here forms the feed to the downstream reaction region. This can occur by means of an overflow. If the individual reaction regions are apparatuses separated from one another, there are, taking capital costs into consideration, from 2 to 4 of these. If more than one reaction region is created within one and the same reactor (eg. by the use of separating sheets of metal), the number of reaction regions can also be greater than 4. In the case of a plurality of reaction regions, the vapors are fed to the reaction regions of a common rectification column whose liquid outflow advantageously goes into the first reaction region.

If this process is carried out using an alkanol having 4–8 carbon atoms, the temperature in the first reaction region is generally 70°–150° C., preferably 80°–130° C., and in the last region 100°–160° C., preferably 110°–130° C. The reaction temperature is preferably set in such a way that it rises along the cascade. The pressure in all reaction regions is from 100 mbar to atmospheric pressure, preferably 200 mbar–700 mbar. The pressure is advantageously the same in all reaction regions. The total residence time of the reactants in the reaction region is 0.5–10 hours, preferably 1–7 hours, particularly preferably 2–5 hours.

As acid esterification catalyst, preference is given to using para-toluenesulfonic acid. Its content in the reaction zone, based on the reaction mixture present therein, is 0.1–10% by weight, preferably 0.1–6% by weight. Acid esterification catalysts such as sulfuric acid and/or other organic sulfonic acids can likewise be used.

In general, both the (meth)acrylic acid and the catalyst are fed directly to the reaction zone. The alkanol to be esterified is preferably fed to the reaction zone via the rectification unit III superposed thereon. This rectification unit III can be a rectification column of a known construction type, for example having bubble cap trays or mesh trays. The reaction regions can advantageously consist of reactors having natural or forced convection vaporizers.

Depending on the alkanol to be esterified, methods of operation differing in detail are appropriate and useful. In the reaction of lower alkanols, the boiling points of the ester and the (meth)acrylic acid are so close together that they can no longer be separated economically by distillation in the rectification unit II; this applies particularly to n-butyl acrylate. For this reason, water is fed into the rectification unit I to keep the (meth)acrylic acid in the liquid phase. The resulting process steps are illustrated by means of the esterification of n-butanol with (meth)acrylic acid.

The esterification of alkanols having more than 4 carbon atoms, in particular those having 8 carbon atoms, in which the boiling points of the ester and (meth)acrylic acid are further apart and addition of water to the rectification unit I is therefore not necessary, are described in more detail by means of the example of the esterification of 2-ethylhexanol.

Hence, the esterification of alkanols having 1–4 carbon atoms with (meth)acrylic acid will first be described for the example of n-butanol as alkanol. Here, the aqueous phase obtained at the top of the rectification unit III is discharged, preferably completely. The product mixture discharged from the reaction zone is fed with addition of water to the rectification unit I. The product mixture introduced with addition of water into this rectification unit I is in the latter separated into a product II comprising the catalyst and the remaining (meth)acrylic acid and a product I comprising the n-butyl ester of (meth)acrylic acid, remaining n-butanol and water. The product containing the water can then be separated into an organic phase comprising the n-butyl ester of (meth)acrylic acid and n-butanol and an aqueous phase. Advantageously, the aqueous phase is then partly returned to the rectification unit I. This rectification unit is configured as a rectification column of the above-described construction type. The product mixture discharged from the reaction zone is fed to the lower part of the rectification column I and the water addition is preferably carried out in the upper part of the rectification column I. In the rectification unit I, a liquid aqueous phase and a liquid organic phase are produced.

Advantageously, part of the resulting organic phase comprising the n-butyl ester of (meth)acrylic acid and n-butanol is returned to the upper part of the rectification column I. The product II which is formed in the rectification unit I and comprises the catalyst and the remaining (meth)acrylic acid can be essentially completely returned to the reaction zone, preferably in the first reaction region, either directly and/or via the rectification unit III. In this procedure, part of the product II formed in the rectification unit I can be discharged and fed to a further distillation unit IV. In this, the product can be separated into a product III comprising n-butanol, (meth)acrylic acid and the n-butyl ester of (meth)acrylic acid and a product IV comprising the catalyst and components having boiling points higher than that of the n-butyl ester of (meth)acrylic acid. The product III comprising n-butanol, (meth)acrylic acid and the n-butyl ester of (meth)acrylic acid can then be returned to the rectification unit I and/or the reaction zone.

The organic phase of the product I is advantageously fed to a rectification unit II and in this is separated into a) a product V comprising remaining n-butanol and components having boiling points lower than that of n-butyl (meth)acrylate, b) the target ester n-butyl (meth)acrylate and c) a product VI comprising constituents having boiling points higher than n-butyl (meth)acrylate. The product V is recirculated to the reaction zone, preferably via the rectification unit III. The product VI is returned to the rectification unit I. The rectification unit II can be configured as a rectification column II of a construction type described above. The above mentioned product V is separated off in the upper part of the rectification column II, the product VI is separated off in the bottom of the rectification column II and the n-butyl (meth)acrylate is taken off in vapor form by means of a lateral offtake in the lower part of the rectification column II. The gaseous target product n-butyl (meth)acrylate is then condensed and can afterwards be admixed with a storage stabilizer.

The esterification with alkanols having 5–8 carbon atoms will now be described by means of the example of the esterification with 2-ethylhexanol. Here, the product mixture discharged from the reaction zone is fed to the rectification unit I. Part of the aqueous phase obtained at the top of the rectification unit III is returned to the rectification unit III. The product mixture fed to the rectification unit I is in this separated into a product VII comprising the 2-ethylhexyl ester of (meth)acrylic acid, remaining 2-ethylhexanol and remaining (meth)acrylic acid and a product VIII comprising the catalyst and components having boiling points higher than that of the 2-ethylhexyl ester of (meth)acrylic acid. Here, a rectification column I is advantageously again used as rectification unit I. The product mixture discharged from the reaction zone is fed to the lower part of this column. The product VIII is obtained from the bottom of this rectification column and the product VII is obtained at the top. Part of the product VIII is advantageously returned to the reaction zone, preferably in the first reaction region, either directly and/or via the rectification unit III. Advantageously, part of the product VIII is discharged and fed to a distillation unit IV and in this is separated into a product IX comprising 2-ethylhexanol, (meth)acrylic acid and the 2-ethylhexyl ester of (meth)acrylic acid and a product X comprising the acid esterification catalyst and components having boiling points higher than that of the 2-ethylhexyl ester of (meth) acrylic acid.

The product IX can then be returned to the rectification unit I and/or to the reaction zone. Acid esterification catalyst can be partially or completely separated from the product VIII and/or the product X by extraction with water and the aqueous phase obtained can be partially or completely returned to the reaction zone. Part of the aqueous phase formed in the rectification unit III can be used for this extraction. The product VII taken from the rectification unit I can be fed to the rectification unit II and in this be separated into a) a product XI comprising remaining 2-ethylhexanol, (meth)acrylic acid and components having boiling points lower than 2-ethylhexyl (meth)acrylate, b) the target ester 2-ethylhexyl (meth)acrylate and c) a product XII comprising constituents having higher boiling points than 2-ethylhexyl (meth)acrylate. The product XI can then be returned to the reaction zone, preferably via the rectification unit III, and the product XII can be returned to the rectification unit I. The rectification unit II is advantageously configured as a rectification column. Here, the product XI can be separated off in the upper part, the product XII from the bottom and the 2-ethylhexyl (meth)acrylate can be taken off in vapor form as a lateral branch stream in the lower part.

Further details and advantages of the invention may be found in the examples described with the aid of the drawings. In the drawings.

Figure 1:
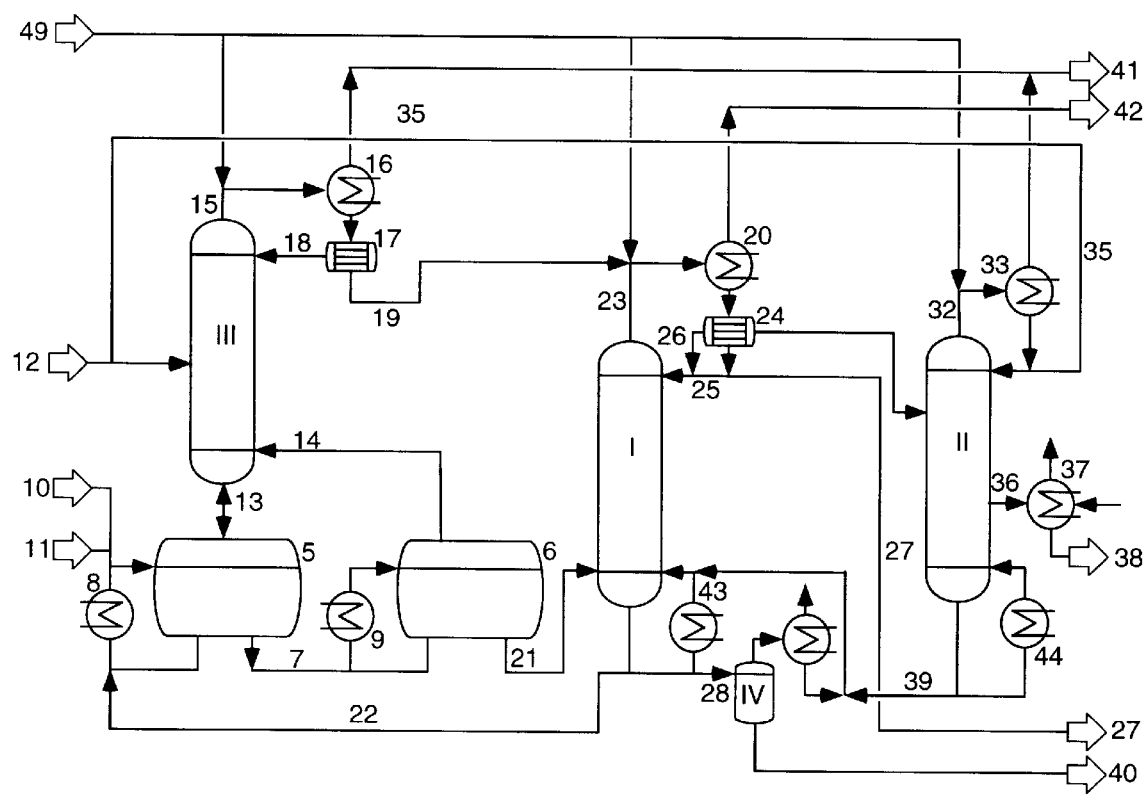
FIG. 1 shows the process flow diagram of a plant for preparing n-butyl acrylate

Equipment items which are the same or have the same action are provided with the same reference numerals. The rectification columns are provided with Roman reference numerals. In the interest of clarity, the product designations, generally provided with Roman numerals, are also inserted specifically in these specific examples.

The plant shown in FIG. 1 for carrying out the process of the present invention for preparing n-butyl acrylate has three rectification columns I, II, III, and a distillation unit IV. It is additionally provided with two esterification reactors 5 and 6 which are connected in series via a line 7 and thus form a reaction cascade. Convection vaporizers 8 and 9 are connected to the reactors 5 and 6. 4 mol/h of acrylic acid were fed via line 10 to the first reactor 5 and 4 mol/h of n-butanol were fed in via the column III superposed on the first reactor 5, the n-butanol being introduced into the column m through the line 12. (For the sake of simplicity, butanol is used hereinafter to refer to n-butanol.) In addition, aqueous para-toluenesulfonic acid as catalyst was introduced via line 11 into the first reactor 5 in an amount of 1.5% by weight, based on the starting materials used. The reaction in the first reactor 5 was carried out at 100° C., in the downstream second reactor 6 at 105° C., at a system pressure of 380 mbar and a residence time in the reaction zone of about 3 hours.

The vapors rising from the reactors 5 and 6 were introduced through lines 13 and 14 into a column III fitted with 25 bubble cap trays and operated at 360 mbar pressure at the top as first rectification unit and rectified therein. The top product of this column III was free of acrylic acid. It was condensed in a surface condenser 16 and conveyed to a separator 17. There, an organic phase containing 70% by weight of butanol, 12% by weight of butyl acrylate, $\leq 13\%$ by weight of water, 4% by weight of butyl acetate and 2000 ppm of dibutyl ether separated out. It was completely returned through line 18 as runback to the column III. The aqueous phase formed in the separation, which still contained 6% by weight of butanol, 300 ppm of butyl acrylate, 750 ppm of butyl acetate, was, for the purpose of increasing the conversion in the reaction, separated off completely and fed via line 19 to the condenser 20 of the downstream rectification column I.

The liquid raw ester flowing out from the second reactor 6 was fed via line 21 to the rectification column I. It contained 78% by weight of the desired product n-butyl acrylate, about 4% by weight each of the unreacted starting materials butanol and acrylic acid and up to 5% by weight of catalyst, as well as 0.2% by weight of water and at most 20 ppm of dibutyl ether. The remainder was high-boiling by-products, in particular oxy ester compounds.

Acrylic acid and high boilers together with a part of the product and of the alcohol were separated off as bottom product (product II) in the rectification column I which was fitted with 25 dual flow trays having a diameter of 50 mm and was operated at ambient pressure. The bottom product (product II) contained 20% by weight of acrylic acid, 45% by weight of butyl acrylate, 3% by weight of butanol, 8% by weight of water. A partial amount of about 45% of the feed amount fed in through line 21 was returned via line 22 to the first reaction region.

The major part of the high boilers (up to 80% of the amount fed in) was here cracked in the liquid phase of the rectification column I to form starting materials and products. Owing to the high acrylic acid and water contents of the bottom product at a bottom temperature of 105° C., only insignificant amounts of low-boiling by-products ($\leq$200 ppm of dibutyl ether) were formed here. These by-products were separated off together with the main product stream as a low-boiling minimum heteroazeotrope via the top of the column I and fed via line 23 to the condenser 20. Both the liquid in the column and the top product here separated at 95° C. into an aqueous phase and an organic phase. To maintain the heteroazeotrope in the column I, this was treated with aqueous phase from the decanter 24 through line 25 and with organic phase from the decanter 24 through line 26 as runback. The aqueous phase contained $\leq$3% by weight of organic constituents, predominantly butanol. The organic phase contained from 75 to 85% by weight of butyl acrylate, from 14 to 20% by weight of butanol, from 2 to 3% by weight of water, 1500 ppm of butyl acetate. The excess water corresponding to the conversion in the reaction was removed from the system through line 27.

5% by weight of the bottom product (product II), based on the amount of starting materials fed to the esterification, were discharged via a line 28 and fed to a wall-heated stirred vessel IV. There, the product was evaporated batchwise at ambient pressure and 180° C. until the viscosity rose distinctly. The starting materials butanol and acrylic acid still present therein and the product butyl acrylate were first distilled off (product III). The amount of distillate was up to about 65% by weight, based on the amount fed in. In the subsequent cracking of the high boilers, which was continued to an amount of distillate of about 85%, based on the amount fed in, low-boiling by-products such as butenes and dibutyl ether were formed to a slight extent only toward the end. The condensed vapor (product IV) from the cracking in the stirred vessel IV consisted essentially of acrylic acid, butyl acrylate, butanol and water. This product was recirculated directly to the bottom of the column I for the high boiler separation. A further rectification was not carried out.

The organic top product (product I) from the azeotropic distillation in the column I, which was free of high boilers and acrylic acid, was fed via line 31 to a distillation column II which was fitted with 25 dual flow trays having a diameter of 50 mm and was operated at a top pressure of 450 mbar and rectified therein. Butanol, residual water and any low boilers present were taken off as top product via line 32 (product V). This contained from 65 to 70% by weight of butanol, from 20 to 30% by weight of butyl acrylate, from 8 to 10% by weight of water, $\leq$500 ppm of dibutyl ether, $\leq$4000 ppm of butyl acetate. This top product (product V) was condensed in a condenser 33 and a partial amount of 60% was returned through line 34 as runback to the top of the rectification column II. The remaining amount was fed through line 35, together with the fresh alcohol fed in through line 12, to the esterification via the first column I. The butyl acrylate was concentrated in the liquid phase of this column II and, to achieve the desired color number and to separate off the process stabilizer, was taken off in vapor form as a lateral branch stream through line 36, condensed in the condenser 37 and conveyed away through line 38. The pure product contained $\leq$50 ppm of butanol, $\leq$50 ppm of dibutyl ether, $\leq$150 ppm of water, $\leq$50 ppm of acrylic acid.

A small bottom bleed stream (product VI) in an amount of $\leq$2% by weight of the feed to the column was conducted via line 39 to the bottom of the high boiler separation in column I.

The residue was discharged from the stirred vessel IV through line 40. Line 41 connected the columns III and II to a vacuum pump. Waste air from the column III was removed through line 42. The liquid phase of the columns I and II was heated via convection vaporizers 43 and 44 respectively.

The pure ester had a purity of $\geq$99.9%, the yield based on acrylic acid and butanol was 98% of theory in each case.

In a further experiment, the second esterification reactor 6 was taken out of operation and the raw ester from the first reactor 5 was introduced via line 7 directly into the bottom of the column I. The reaction was carried out at 105° C. Using feed flows the same as in the variant with two reactors, and thus a reduced residence time, and otherwise identical process parameters, it was possible to obtain a raw ester containing 71% by weight of the desired product n-butyl acrylate, 0.4% by weight of water, at most 20 ppm of dibutyl ether, about 7% by weight of each of the starting materials (butanol and acrylic acid) and up to 5% by weight of catalyst. The remainder was high-boiling by-products, in particular oxy ester compounds.

The raw ester thus produced was purified by a method similar to the first experiment at identical process parameters in the work-up part to give a 99.9% pure product in a total yield of 98%, based on the starting materials.

Figure 2:
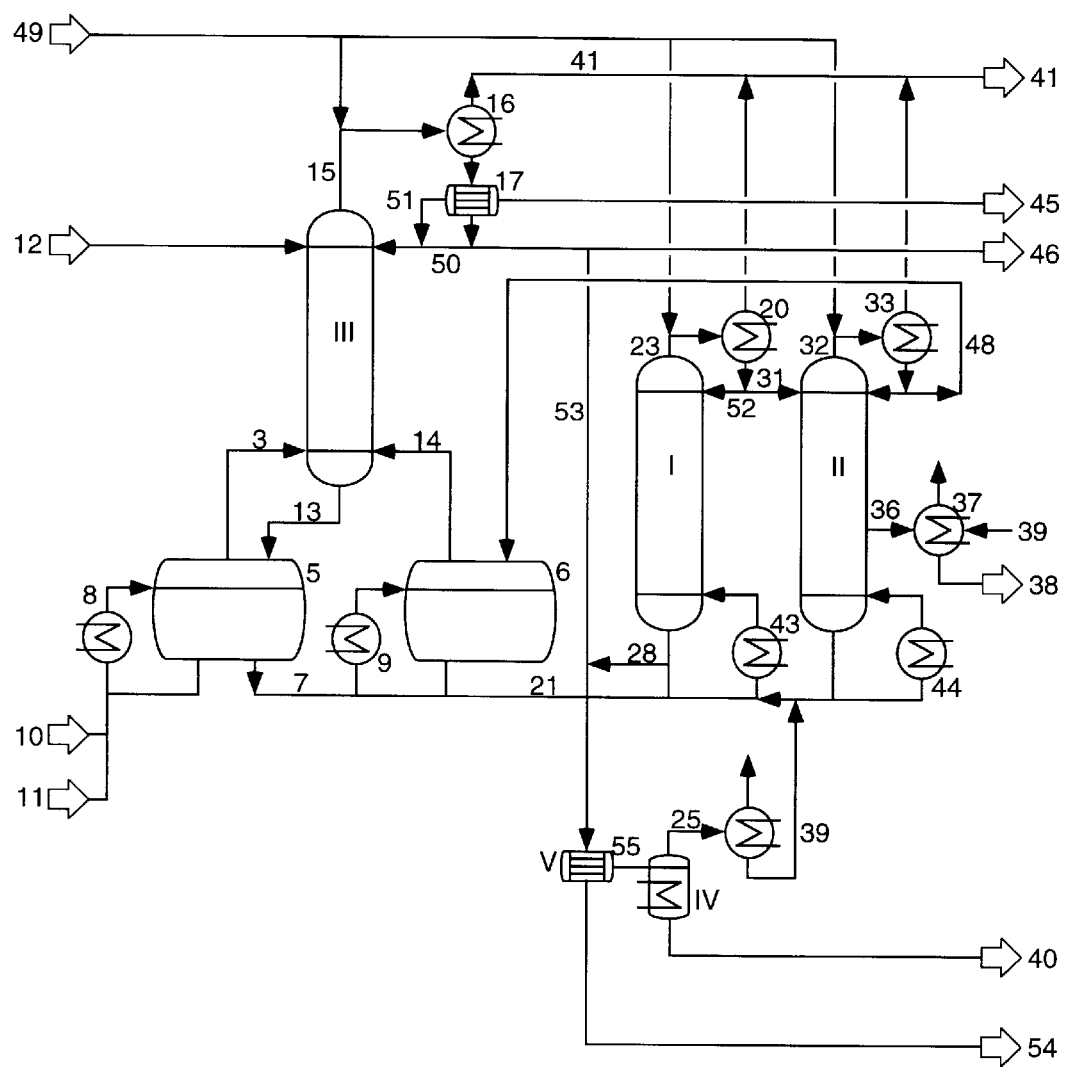
FIG. 2 shows the process flow diagram of a plant for producing 2-ethylhexyl acrylate.

The plant shown in FIG. 2 for carrying out the process of the present invention was used to prepare 2-ethylhexyl acrylate.

The esterification reaction for reacting 2-ethylhexanol and acrylic acid was carried out in a two-stage esterification cascade consisting of two reactors 5 and 6 each having the same volume. Acrylic acid was fed to the reactor 5 via a line 10 and p-toluenesulfonic acid as catalyst was fed via line 11 to a convection vaporizer 8. The reaction component 2-ethylhexanol was fed via a line 12 to the top of a distillation column III whose lower end was connected via line 13 to the reactor 5. The vapor formed in the esterification in the reactors 5 and 6 and comprising the water of reaction was fed via lines 3 and 14 to the distillation column III which had ten theoretical plates and was operated at a pressure of 270 mbar. This pressure was maintained by means of a line 15 which led to a condenser 16 and a line 41 leading to a vacuum pump. The condensate formed in the condenser 16 was separated in the separator 17 into two liquid phases. Octenes separated off were conveyed away through line 45. Water of reaction was conveyed away through line 46.

Since the starting materials were fed at ambient temperature to the reactor 5 and a large amount of water is formed in the reaction, a high heat input into the first reactor 5 is necessary to maintain a reaction temperature of 110° C. This makes possible the use of an external convection vaporizer 8 which is also particularly advantageous in terms of the necessary mixing of the contents of the vessel. The bottom product discharged from the reactor 5 via line 7 was fed via a further convection vaporizer 9 to the second reactor 6 in which a temperature of 120° C. was set. The second vaporizer 9 was also configured as a convection vaporizer to ensure, despite a significantly lower heat input, a sufficient circulation flow for mixing of the contents of the vessel. Here too, lean air was added as costabilizer. In accord with the decreasing acrylic acid and water concentrations, the second reactor 6 was operated at elevated temperature. The bottom product formed in the reactor 6 was discharged through line 21. The total material discharged from the reaction, which contains the target product, ie. the 2-ethylhexyl acrylate formed, and all lower-boiling starting materials and by-products, was introduced, via line 21 and a further convection vaporizer 43, into the lower part of a rectification column I which was configured as an enrichment column and, being fitted with ten dual flow trays, served for the high boiler separation. The target product, namely 2-ethylhexyl acrylate, and all lower-boiling starting materials and by-products (product VII) were discharged via the top through line 23 and, after flowing through a condenser connected to the vacuum line 41 were fed via line 31 to the top of a pure column II operated as a stripping column.

The column I for the high boiler separation was operated at a bottom pressure of 100 mbar and a top pressure of 70 mbar. The temperature was 150° C.

The bottoms (product VIII) formed in the column I for the high boiler separation was discharged via a line 28, cooled to 50° C. and fed to an extraction unit. The para-toluenesulfonic acid content of the organic phase was lowered to the value of 1.5% optimum for the cracking by addition of a part of the water of esterification through line 53. The water stream flowing out, which contained up to 30% of para-toluenesulfonic acid, was taken off through line 54, the organic phase was taken off through line 55 and fed to a distillation unit IV. In the latter, product still present was first vaporized batchwise at 180° C. and a pressure of 60 mbar. Subsequently, the residue which had a high content of para-toluenesulfonic acid and oxy esters was cracked to form starting materials, target product, water and the octenes obtained as by-product. The combined top product from the cracking was taken off via line 25, liquified and returned via line 39 to the bottom of the high boiler separation. The remaining viscous residue was taken off through line 40 and disposed of in a residue incineration facility.

From the product (product VII) fed via the top to the pure column II through line 31, the starting materials still present and lower-boiling secondary components were taken off via line 32 (product XII) and fed to a condenser 33. The condensate thus formed was returned via line 48 to the second stage 6 of the esterification cascade. The liquid phase of the column II was heated by means of a convection vaporizer 44 similar to those used in the esterification.

The pure product 2-ethylhexyl acrylate was taken off in vapor form via line 36 and fed via a scrubber demister to the pure product condenser 37 in order to avoid color number problems and to make possible the change in stabilization of the product from phenothiazine as process inhibitor to hydroquinone monomethyl ether as storage stabilizer. The pure product was conveyed away through line 38. The storage stabilizer was fed in through line 39. The phenothiazine used as process inhibitor was fed via line 49 to the tops of the rectification columns I, II, III.

A specific example carried out using an experimental apparatus as shown in FIG. 2 will now be described. In this example, use was made of two esterification reactors 5 and 6 each having a utilizable capacity of 2 l which had superposed on them a glass tray column having a diameter of 50 mm and fitted with 20 bubble cap trays as well as a phase separator at the top of the column. The operating pressure was 270 mbar. Convection vaporizers were used to heat the esterification reactors. At a residence time of 4 hours, acrylic acid was reacted with 2-ethylhexanol in the stoichiometric ratio with addition of 1.5% by weight of aqueous p-toluenesulfonic acid and with continuous distillative removal of the water of reaction formed to give 2-ethylhexyl acrylate (EHA). The temperature in the first esterification reactor 5 was 110° C., in the second esterification reactor 6 it was 120° C. An EHA concentration of 70% by weight was achieved in the outflow from the first reactor 5 and a concentration of 82% by weight was achieved in the outflow from the second reactor 6. Low-boiling secondary components (mainly octenes formed in the cracking) were concentrated at the top of the esterification column III to such an extent that the waste stream taken off via line 45 contained only <10% of useful components, ie. 2-ethylhexanol and 2-ethylhexyl acrylate. By means of aqueous column runback, two aqueous phases were generated over the entire height of the column. This enabled the acrylic acid at the top of the column to be depleted to <100 ppm. The water of esterification formed in a stoichiometric amount contained about 1.5% of organic compounds (mainly 2-ethylhexanol and octenes) at equilibrium.

The esterification product discharged through line 21 was freed of the catalyst acid and the high boilers formed in a laboratory column I having a diameter of 50 mm, fitted with 10 dual flow trays and equipped with convection vaporizer and upright tube-bundle condenser. 5% of the amount of raw ester fed in was taken off at a reflux ratio of 0.5 from the bottom of the column as high-boiler bleed and fed to the cracking step, while the remainder was taken off as top product free of high boilers (oxy esters <10 ppm). The feed to the column was directly to the bottom of the column and the column I was operated purely as an enrichment column. At a top pressure of 80 mbar, the bottom temperature was able to be kept at a maximum of 150° C. The top product, which was free of high boilers, was separated in a laboratory column II having a diameter of 50 mm, equipped with 25 dual flow trays at a top pressure of 80 mbar and having a maximum bottom temperature of 140° C. to give a top fraction comprising the starting materials acrylic acid and 2-ethylhexanol and 50% by weight of 2-ethylhexyl acrylate plus the pure product. The top fraction was returned to the second esterification reactor 6. The pure product was taken off in vapor form and free of high boilers and process stabilizers from the bottom of the column which was heated using a natural convection vaporizer and liquified in a condenser regulated by inert blanketing. A content of >99.8% by weight of 2-ethylhexyl acrylate was thus achieved. Accumulation of high-boiling trace components in the liquid phase in the column was prevented by taking off an amount of liquid at the bottom of the column corresponding to 2% of the amount of liquid flowing in and feeding it to the bottom of the high boiler separation stage. The bottom discharge of the high boiler separation stage was, after partial extraction of the catalyst acid with water, evaporated to 20% of its original mass in a cracking vessel IV operated batchwise at 60 mbar and a maximum temperature of 180° C. The resulting residue contained the catalyst acid p-toluenesulfonic acid and also a high concentration of high boilers which could not be cracked or vaporized. This residue could not be utilized further in the process and was taken off. The top product comprising 80% of EHA, from 10 to 12% of octenes and also acrylic acid, water and 2-ethylhexanol was condensed in a heat exchanger and returned to the bottom of the high boiler separation stage.

A yield of 98% based on starting materials was able to be achieved in continuous, steady-state operation of this experimental unit. Only 2% of the starting materials used were lost as by-products.

The stabilizer solution used was a 2% strength phenothiazine solution in 2-ethylhexanol which was metered into the top condensers of the individual process stages in an amount of 100 ppm based on the respective feed stream to the stage. All natural convection vaporizers were exposed to air as costabilizer.

A particular advantage of the above-described process is the removal of all high-boiling secondary components and, in particular, the catalyst from the esterification product in column I. This reliably avoids redissociation of the high boilers and/or the target product in the liquid phase of the pure column II to form starting materials and thus prevents contamination of the pure product with low-boiling dissociation products and, in particular, acrylic acid.

If, as is customary in conventional procedures, the components having boiling points lower than that of the target ester (in particular acrylic acid and starting alkonol) are first separated from the esterification product, it is not possible to isolate pure product free of low boilers and in particular free of acrylic acid owing to the dissociation reactions which then occur in the liquid phase of the pure column in the presence of catalyst and high boilers, as was demonstrated by the example described below.

Esterification product taken from line 21 was first, in column I, freed of all secondary components having boiling points lower than that of the target ester and also freed of the starting materials acrylic acid and 2-ethylhexanol. From the bottom of the column I, the raw ester free of low boilers but contaminated with high boilers and, in particular, the catalyst was then taken off and rectified at a reflux ratio of 2 in a laboratory column having a diameter of 50 mm and equipped with 25 dual flow trays. The raw ester taken off from the top of the column was then contaminated with 1400 ppm of acrylic acid although the raw ester fed in was free of acrylic acid; ie. the acrylic acid found in the target ester can only have arisen by means of dissociation reactions in the liquid phase of the column. However, distillative removal of the acrylic acid is not possible when the pure ester is isolated as top product, since acrylic acid is a low boiler in comparison with the target ester.

The above-described experimental results and further studies showed that it is advantageous to operate the two esterification reactors 5 and 6 at pressures of from 180 to 500 mbar, preferably from 180 to 350 mbar. The temperature in the first reactor 5 can be from 80° to 120° C., in the second reactor 6 from 100° to 140° C. As catalyst for the esterification reaction in the reactors 5 and 6, acid catalysts, in particular organic sulfonic acids and here particularly p-toluenesulfonic acid in an amount of from 0.1 to 4% by weight, preferably from 0.5 to 2% by weight, have been found to be particularly advantageous.

The residence time of (meth)acrylic acid and alkanol in the reactors is from 0.5 to 8 hours, preferably from 1 to 6 hours. From the raw ester fed to the rectification column I through line 21, it is possible, at a reflux ratio of 0.5, to take off an amount of <10% by weight, preferably <5% by weight, from the bottom of the column as high-boiler bleed and pass it to the cracking step. The top pressure of the column I can be from 50 to 400 mbar, preferably <120 mbar. The maximum bottom temperature of this column is preferably $\leq 150°$ C. The top product of column I, which is free of high boilers and was fed via line 26 to the column II, can be processed in the latter column at a top pressure of from 50 to 400 mbar, preferably at a pressure of <120 mbar, and at a bottom temperature of <140° C. With optimum setting of the abovementioned values, a product containing >99.8% by weight of pure product, in the case of the example 2-ethylhexyl acrylate, can be taken off through line 36.

We claim:

1. A process for the continuous preparation of alkyl esters of (meth)acrylic acid by reacting (meth)acrylic acid with monohydric alkanols having from 1 to 8 carbon atoms in the presence of an acid esterification catalyst in a reaction zone, in which there is discharged from the reaction zone a product mixture which comprises the alkyl (meth)acrylate formed, the catalyst and the by-products formed during the course of the esterification having boiling points higher than that of the alkyl (meth)acrylate, and from which the alkyl (meth)acrylate is separated by distillation in a separation zone, wherein the product mixture discharged from the reaction zone is fed to a rectification unit (I), in this unit the product mixture discharged is separated by rectification into at least one product (I) comprising the alkyl ester of (meth)acrylic acid and a product (II) comprising the catalyst, the product (I) is fed to a further rectification unit (II) and in this the alkyl ester of (meth)acrylic acid is separated off by rectification.

2. A process as claimed in claim 1, wherein the esterification in the reaction zone is carried out in a homogeneous, liquid, solvent-free phase at elevated temperature by reaction of (meth)acrylic acid and an alkanol, having from 4 to 8 carbon atoms, in a molar ratio of from 1:0.75 to 1:2, in such a way that the (meth)acrylic acid, the alkanol and the catalyst are fed to the reaction zone, the water formed is removed by rectification during the residence time as constituent of a mixture comprising alkanol via the top of a rectification unit (III) superposed on the reaction zone, the distillate thus obtained is separated into an organic phase comprising alkanol and an aqueous phase comprising water, the organic phase is returned to the rectification unit (III), and the product mixture is discharged from the reaction zone and fed to a separation zone, wherein the reaction zone comprises a cascade of at least two reaction regions connected in series and the output stream of a reaction region forms a feed stream of a downstream reaction region, and wherein the cascade has from 2 to 4 reaction regions separated from one another in space.

3. A process as claimed in claim 1, wherein the rising vapors from the reaction regions are fed to a single rectification unit whose liquid runback is returned only to the first reaction region.

4. A process as claimed in claim 2, wherein the temperature in the first reaction region is from 70° to 150° C., and in the last region is from 100° to 160° C., and wherein the reaction temperature rises along the cascade.

5. A process as claimed in claim 2, wherein the pressure in all reaction regions is from 100 mbar to atmospheric pressure, preferably from 200 mbar to 700 mbar, especially is the same in all reaction regions.

6. A process as claimed in claim 1, wherein the catalyst used is selected from the group consisting of para-toluenesulfonic acid, methanesulfonic acid, benzenesulfonic acid, dodecylbenzenesulfonic acid and sulfuric acid, and mixtures thereof and wherein the content of catalytically active acid in the reaction zone, based on the reaction mixture present therein, is from 0.1 to 10% by weight, of paratoluenesulfonic acid or an amount equimolar thereto of another organic sulfonic acid and/or sulfuric acid.

7. A process as claimed in claim 1, wherein both the (meth)acrylic acid and the catalyst are fed directly to the reaction zone, and alkanol, to be esterfied is n-butanol and is fed to the reaction zone via the rectification unit (III), the rectification unit (III) is a rectification column, and wherein the reaction regions comprise reactors having convection vaporizers.

8. A process as claimed in claim 7, wherein the aqueous phase obtained at the top of the rectification unit (III) is essentially completely discharged, the organic phase formed is essentially completely returned to the rectification unit (III), the product mixture discharged from the reaction zone is fed with addition of water to the rectification unit (I), wherein the product mixture fed with addition of water to the rectification unit (I) is in the latter separated into a product (II) comprising the catalyst and the remaining (meth)acrylic acid and a product (I) comprising the n-butyl ester of (meth)acrylic acid, remaining n-butanol and water, and which furthermore is separated into an organic phase comprising the n-butyl ester of (meth)acrylic acid and n-butanol and an aqueous phase.

9. A process as claimed in claim 8, wherein aqueous phase is returned to the rectification unit (I), a liquid aqueous phase and a liquid organic phase are present in the rectification unit (I), the rectification unit (I) is a rectification column (I), the product mixture discharged from the reaction zone is fed to the lower part of the rectification column (I) and the addition of water is carried out in the upper part of the rectification column (I), and wherein part of the resulting organic phase comprising the n-butyl ester of (meth)acrylic acid and n-butanol is returned to the upper part of the rectification column (I).

10. A process as claimed in claim 8, wherein the product (II) which is formed in the rectification unit (I) and comprises the catalyst and the remaining (meth)acrylic acid is essentially completely returned to the reaction zone, preferably in the first reaction region, either directly and/or via the rectification unit (III), at least a part of the product (II) formed in the rectification unit (I) is discharged and fed to a distillation unit (IV) and in this is separated into a product (III) comprising n-butanol, (meth)acrylic acid and the n-butyl ester of (meth)acrylic acid and a product (IV) comprising the acid esterification catalyst and components having boiling points higher than that of the n-butyl ester of (meth)acrylic acid, the product (III) is returned to the rectification unit (I) and/or the reaction zone, wherein the organic phase of the product (I) is fed to a rectification unit (II) and in this is separated into a) a product (V) comprising remaining n-butanol and components having boiling points lower than that of n-butyl (meth)acrylate, b) n-butyl (meth)acrylate and c) a product (VI) having a boiling point higher than n-butyl (meth)acrylate, the product (V) is returned to the reaction zone, preferably via the rectification unit (III), the product (VI) is returned to the rectification unit (I), the rectification unit (II) is a rectification column (II), and wherein the product (V) is separated off in the upper part of the rectification column (II), the product (VI) is separated off from the bottom of the rectification column (II) and the n-butyl (meth)acrylate is taken off in vapor form as a lateral branch stream in the lower part of the rectification column (II).

11. A process as claimed in claim 1, wherein the alkanol used is 2-ethylhexanol, wherein part of the aqueous phase obtained at the top of the rectification unit (III) is returned to the rectification unit (III), the product mixture discharged from the reaction zone is fed to the rectification unit (I), wherein the product mixture fed to the rectification unit (I) is separated in the rectification unit (I) into a product (VII) comprising the 2-ethylhexyl ester of (meth)acrylic acid, remaining 2-ethylhexanol and remaining (meth)acrylic acid and a product (VI) comprising the catalyst and components having boiling points higher than that of the 2-ethylhexyl ester of (meth)acrylic acid, the product mixture charged from the reaction zone is fed to the lower part of the rectification column (I), and wherein the product (VIII) is obtained from the bottom of the rectification column (I) and the product (VII) is obtained at the top of the rectification column (I).

12. A process as claimed in claim 11, wherein part of the product (VIII) is returned to the reaction zone, preferably in the first reaction region, either directly and/or via the rectification unit (III), wherein part of the product (VIII) is discharged and fed to a distillation unit (IV) and in this is separated into a product (IX) comprising 2-ethylhexanol, (meth)acrylic acid and the 2-ethylhexyl ester of (meth) acrylic acid and a product (X) comprising the catalyst and components having boiling points higher than that of the 2-ethylhexyl ester of (meth)acrylic acid, the product (IX) is returned to the rectification unit (I) and/or the reaction zone, wherein catalyst is separated from the product (VIII) and/or the product (X) by extraction with water and the aqueous phase obtained is returned to the reaction zone, and wherein part of the aqueous phase formed in the rectification unit (III) is used for the extraction.

13. A process as claimed in claim 11, wherein the product (VII) taken from the rectification unit (I) is fed to a rectification unit (II) and in this is separated into a) a product (XI) comprising remaining 2-ethylhexanol and components having boiling points lower than that of 2-ethylhexyl (meth)acrylate, b) 2-ethylhexyl (meth)acrylate and c) a product (XII) having a boiling point higher than 2-ethylhexyl (meth)acrylate, wherein the product (XI) is returned to the reaction zone, via the rectification unit (III), the product (XII) is returned to the rectification unit (I), the product (XI) is separated off in the upper part of the rectification column (II), the product (XII) is separated off from the bottom of the rectification column (II) and the 2-ethylhexyl (meth)acrylate is taken off in vapor form as a lateral branch stream in the lower part of the rectification column (II), and wherein part of the organic phase formed in the rectification unit (III) is bled off to remove low-boiling by-products from the system.

14. The process as set forth in claim 2, wherein the molar ratio of (meth)acrylic acid and alkanol is from 1:0.9 to 1:1.1.

15. The process as set forth in claim 2, wherein the molar ratio of (meth)acrylic acid and alkanol is 1:1.

16. The process as set forth in claim 4, wherein the temperature in said first reaction region is from 80° to 130° C. and the temperature in said last region is from 110° to 130° C.

17. A process as set forth in claim 6, wherein the content of catalytically active acid in the reaction zone, based on the reaction mixture present therein, is from 0.1 to 6% by weight.

18. A process as set forth in claim 2, wherein separated aqueous phase is returned to the rectification unit (III).

* * * * *